US00PP12957P2

(12) United States Plant Patent
Noodelijk

(10) Patent No.: US PP12,957 P2
(45) Date of Patent: Sep. 17, 2002

(54) CHRYSANTHEMUM PLANT NAMED 'TETON'

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 0 days.

(21) Appl. No.: 09/276,701

(22) Filed: Mar. 26, 1999

(51) Int. Cl.[7] ..... A01H 5/00
(52) U.S. Cl. ..... Plt./295
(58) Field of Search ..... Plt./295

(56) References Cited

PUBLICATIONS

UPOV–ROM GTITM Computer Database 2000/06, Dec. 8, 2000, GTI Jouve Retrieval Software, citation for 'Teton'.*

* cited by examiner

*Primary Examiner*—Bruce R. Campell
*Assistant Examiner*—June Hwu
(74) *Attorney, Agent, or Firm*—Parkhurst & Wendel, L.L.P

(57) ABSTRACT

A chrysanthemum plant named 'Teton' characterized by its small sized bloom with yellow ray-florets.

2 Drawing Sheets

BACKGROUND OF THE INVENTION

'Teton' is a product of a breeding-program which had the objective of creating new chrysanthemum cultivars with a anemone type flower, a 7 week response and a compact plant height. The new plant of the present invention comprises a new and distinct cultivar of Chrysanthemum plant. 'Teton' is a seedling from a cross in a breeding program maintained under the control of inventor. The female parent is # 90.0933-unpatented-, an unnamed seedling not available to inventor for description. The male parent is unknown, being a mixed population of a group of male parents. The new and distinct cultivar was discovered and selected as a flowering plant within the progeny of the stated cross by Rob Noodelijk in a controlled environment (greenhouse) in Rijsenhout Holland in May 1995. The first act of asexual reproduction of 'Teton' was accomplished when vegetative cuttings were taken from the initial selection in August 1995 in a controlled environment in Rijsenhout Holland.

SUMMARY OF THE INVENTION

The present invention is a new and distinct variety of chrysanthemum bearing small sized blooms with yellow ray-florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
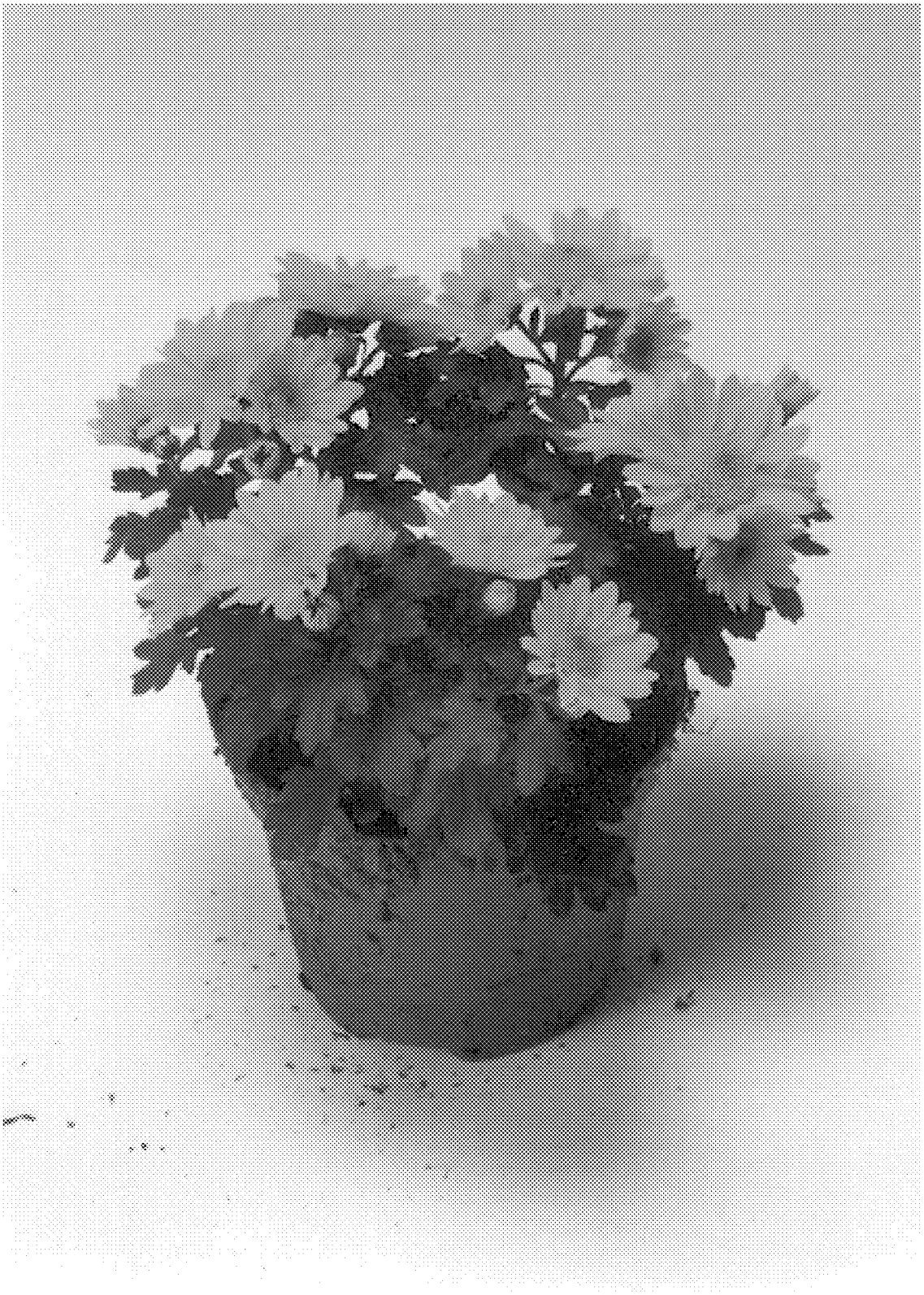
FIG. 1 shows a plant of the cultivar in full bloom.
Figure 2:
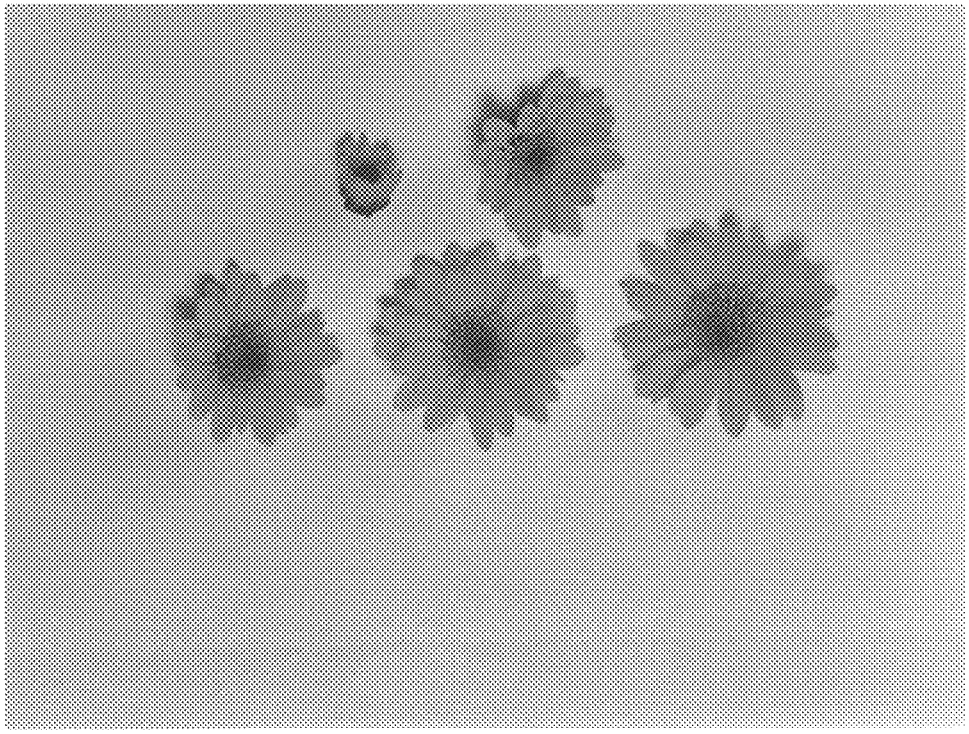
FIG. 2 shows the various stages of bloom of the new cultivar.
Figure 3:
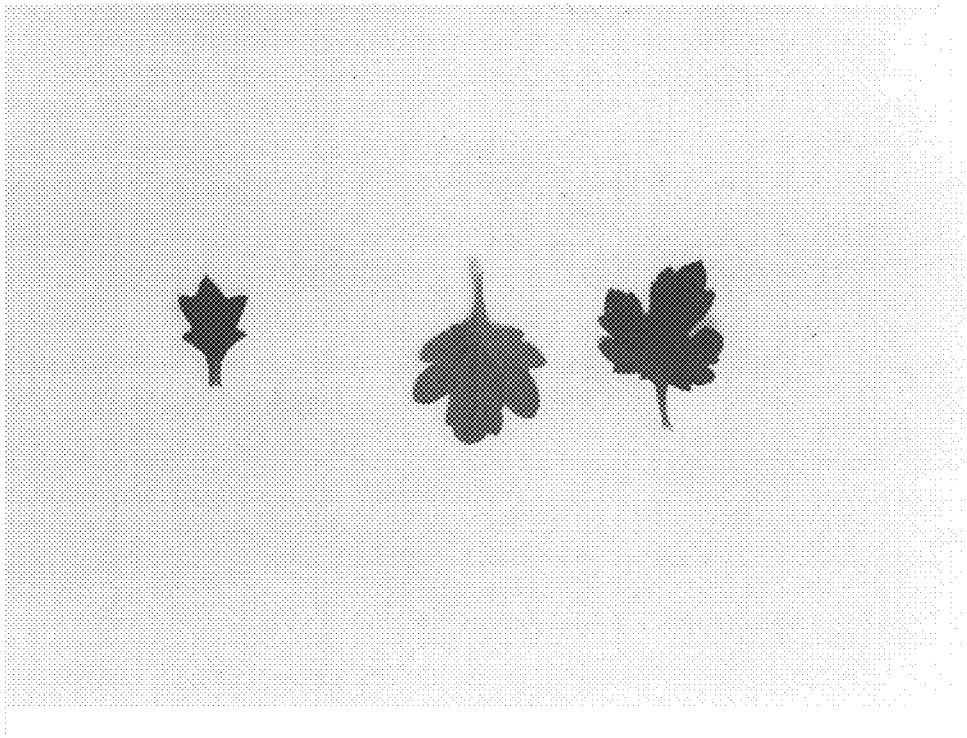
FIG. 3 shows the foliage of the new cultivar.

This new variety of chrysanthemum is of the botanical classification *Dendranthema grandiflora*. The observations and measurements were gathered from plants grown in a greenhouse in Rijsenhout Holland in a photo-periodic controlled crop under conditions generally used in commercial practice. The photo-periodic response time in this crop was 49 days after an average of eight long days. After this long day period to flowering growth retardants were applied 6 times in an average dose of 1.5 gram/liter water. This new variety produces small sized blooms with yellow ray-florets blooming on the plant for 5 weeks. This new variety of chrysanthemum has been found to retain its distinctive characteristics throughout successive propagations however the phenotype may vary significantly with variations in environment such as light intensity and temperature. To show the phenotype as described 'Teton' can be planted without assimilation lightning (high pressure sodium lamps) between week 50 and week 40 of the next year under greenhouse conditions in Holland. With assimilation lightning (minimum level 2500 lux) it can be planted year round under greenhouse conditions in Holland.

From the cultivars known to inventor the most similar existing cultivar in comparison to 'Teton' is 'Indio' (U.S. Plant Pat. No. 6,774). When 'Indio' and 'Teton' are being compared the following differences are noticed: The differences of 'Indio' and 'Teton' are: (1) Response time. The Response time of 'Teton' is shorter. (2) Growth rate/vigor. The plant of 'Teton' is more compact. (3) Flower form and size. The flower of 'Teton' is smaller and the form is a clear anemone with a well pronounced cushion.

The following is a description of the plant and characteristics that distinguish 'Teton' as a new and distinct variety.

The color designations are taken from the plant itself. Accordingly, any discrepancies between the color designations and the colors depicted in the photographs are due to photographic tolerances.

Table 1: Botanical Description of CULTIVAR 'Teton'

Bud:

*Size.*—Small; cross-section 0.9 cm, length 0.7 cm.
*Outside color.*—Yellow 9 B.
*Involucral bracts.*—2 rows, length 7 mm, width 3 mm.

*Involucral bracts among disc-florets.*—Not present.
*Involucral bracts color.*—Yellow-green 146B.

Bloom:
*Type.*—Anemone.
*Height.*—Flat.
*Size.*—Small.
*Fully expanded.*—4.0–4.5 cm.
*Borne* (*number of blooms per branch*).—Approx. 6 blooms per branch.
*Performance on the plant.*—5 weeks.
*Seeds.*—Not produced.
*Fragrance.*—Typical chrysanthemum.

Color:
*Center of the flower* (*disc-florets*).—Immature 146 B with 13 A along the edge. Mature 151 B with the outer border 13 A.
*Color of upper surface of the majority of the ray-florets.*—Yellow 9 A.
*Color of the lower surface of the majority of the ray-florets.*—Yellow 6 C.
*Tonality from distance.*—A pot mum with small yellow flowers.
*Discoloration to color.*—Yellow 7 A.

Ray florets:
*Texture.*—Upper and under side smooth.
*Number.*—36–40.
*Cross-section.*—Concave.
*Longitudinal axis of majority.*—Straight.
*Length of corolla tube.*—Short.
*Ray-floret margin.*—Entire.
*Ray-floret length.*—1.8–2.0 cm.
*Ray-floret width.*—0.8 cm.
*Ratio length/width.*—Low.
*Shape of tip.*—Acute.

Disc florets:
*Disc diameter.*—1.5 cm.
*Distribution of disc florets.*—Numerous and visible at all stages of flowering.
*Type.*—Petaloid.
*Color.*—Yellow 7 C.
*Receptacle shape.*—Conical raised.

Reproductive organs:
*Stamen* (*present in disc florets only*).—Yellow-green 146B, thin, 3 mm in length.
*Pollen.*—Appears late.
*Pollen color.*—Yellow 13 A.
*Styles* (*present in both ray and disc florets*).—Yellow-green 146B, thin.
*Style length.*—4 mm.
*Stigmas.*—Yellow 13A.
*Stigma width.*—1 mm.
*Ovaries.*—Enclosed in calyx.

Plant:
*Form.*—A pot mum meant for indoor use.
*Growth habit.*—Spreading.
*Growth rate.*—Slow.
*Height.*—20.0–22.0 cm.
*Width.*—24.0 cm.
*Stem color.*—Yellow-green 146 B.
*Stem strength.*—Strong.
*Stem brittleness.*—Absent.
*Stem anthocyanin coloration.*—Present to a layer of red on the stem.
*Length of lateral branch.*—From top to bottom 9.0 cm.
*Lateral branch color.*—Yellow-green 146 B.
*Lateral branch, attachment.*—Medium, not weak not strong.
*Branching* (*average number of lateral branches*).—Good with 5 breaks after pinching.
*Peduncle length.*—2.5–3.0 cm.
*Peduncle color.*—Yellow-green 146 B.
*Flowering response* (*photo-periodic controlled crop, no natural growing*).—49 Days.

Foliage:
*Color.*—Upper side green 137 A. Under side green 138 B.
*Size.*—Small; length 4.5 cm, width 3.5 cm.
*Quantity* (*number per lateral branch*).—6–8.
*Shape.*—Ovate and pinnately lobed.
*Texture upper side.*—Fleshy and glabrous.
*Texture under side.*—Pubescent.
*Ribs and veins upper side.*—Ribs and veins well developed.
*Ribs and veins upper side.*—Ribs and veins well developed.
*Venation arrangement.*—Palmate.
*Shape of the margin.*—Crenated.
*Shape of base of sinus between lateral lobes.*—Rounded.
*Margin of sinus between lateral lobes.*—Converging.
*Shape of base.*—Attenuate.
*Apex.*—Cuspidate.
*Age.*—57 days.

TABLE 2

Differences with the comparison varieties

| | 'Teton' | 'Indio' |
|---|---|---|
| Response time | 49 days | 54 days |
| Growth rate | Slow, compact plant | Medium vigor, tall plant |
| Flower form | Anemone with a clear "cushion" | A very compact cushion giving the impression of a daisy type flower |

I claim:

1. A new and distinct variety of chrysanthemum plant as described and illustrated.

* * * * *